United States Patent
Watanabe et al.

[11] Patent Number: 6,087,395
[45] Date of Patent: Jul. 11, 2000

[54] ISOCARBACYCLIN DERIVATIVES AS APOPTOSIS INHIBITORS

[75] Inventors: Yasuyoshi Watanabe, Osaka; Atsuo Hazato, Tokyo; Masaaki Suzuki, Aichi; Yumiko Watanabe; Takumi Sato, both of Osaka, all of Japan

[73] Assignees: Japan Science and Technology Corporation, Saitama; Atsuo Hazato, Tokyo, both of Japan

[21] Appl. No.: 09/173,758

[22] Filed: Oct. 16, 1998

[30] Foreign Application Priority Data

Oct. 21, 1997 [JP] Japan .................................. 9-288912

[51] Int. Cl.[7] .......................... A01N 37/08; A01N 43/00; C07C 62/06
[52] U.S. Cl. ............................. 514/530; 562/466
[58] Field of Search .............................. 562/466; 514/530

[56] References Cited

FOREIGN PATENT DOCUMENTS 8-245498  9/1996  Japan .

OTHER PUBLICATIONS

Cell Growth and Apoptosis; G.P. Studzinski, Ed.; Oxford University Press, Oxford ; pp. 119–167, 1995.

Fujita et al.; Bioorganic & Medicinal Chemistry Letters; 5; (16); pp. 1857–1860, 1995.

Sei Y., et al., Internucleosomal DNA fragmentation in gebil hippocamus following forebrain ischemia. Neurosci. Lett. 171 (1994) 179–182.

Kihara S., et al., Visualization of DNA double strand break in the gerbil hippocampal CA1 following transient ischemia. Neurosci. Lett. 175 (1994) 133–136.

Maeda M., et al., Single strand DNA as an immunocytochemical marker for apoptotic change of ischemia in the gerbil hippocampus. Neurosci. Lett. (1998) 69–72.

Iwai T., et al. Temporal profile of nuclear DNA fragmentation in situ ingerbil hippocampus following transient forebrain ischemia. Brain Res. 671 (1995) 305–308.

Nitatori T., et al., Delayed neuronal death in the CA1 pyramidal cell layer of the gerbil hippocampus following transient ischemia is apoptosis. J. Neurosci. 15 (1995) 1001–1011.

Himi T., et al., A caspase inhibitor blocks ischemia–induced delayed neuronal death in the gerbil. Eur. J. Neurosci. 10 (1998) 777–781.

Hara A., et al., Protective effect fo apoptosis–inhibitory agent, N–tosyl–L–phenylalanyl chloromethyl ketone against ischemia–induced hippocampal neuronal damage. J. Cereb. Blood Flow Met. 18 (1998) 819–823.

Kinoshita M., et al., Up–regulation of the Nedd2 gene encoding an ICE/Ced–3–like cycteine protease in the gerbil brain after transient global ischemia. J. Cereb. Blood Flow Met. 17 (1997) 507–514.

Antonawich FJ et al., Bcl–x1 Bax interaction after transient globlal iscmhemia. J. Cereb. Blood Flow Met. 18 (1998) 882–886.

Aronica EM et al., Aurintricarboxylic acid prevents GLUR2 mRNA down–regulation and delayed neurodegeneration in hippocampal CA1 neurons of gerbil after global ischemia. Proc. Natl. Acad. Sci. USA. 95 (1998) 7115–7120.

Deshmukh JB and Johnson EM Jr., Programmed cell death in neurons; focus on the pathway of nerve growth factor deprivation–induced death of sympathetic neurons. Mol. Pharmacol. 51 (1997) 897–906.

*Primary Examiner*—Gary Geist
*Assistant Examiner*—Robert W. Deemie
*Attorney, Agent, or Firm*—Wenderoth, Lind & Ponack, L.L.P.

[57] ABSTRACT

The present invention provides an apoptosis inhibitor containing a 15R-isocarbacyclin derivative or a 15-deoxy-isocarbacyclin derivative, which can be manufactured easily and economically by means of chemical synthesis.

6 Claims, 4 Drawing Sheets

ISOCARBACYCLIN DERIVATIVES AS APOPTOSIS INHIBITORS

BACKGROUND OF THE INVENTION

1. Field of the Invention

The present invention relates to an apoptosis inhibitor. More particularly, relates to a novel apoptosis inhibitor containing isocarbacyclin derivative, which has been known as a ligand specific to prostacyclin receptors of the central nervous system. The inhibitor has an excellent inhibiting action to apoptosis of nerve cells, etc.

2. Description of the Related Art

Apoptosis is a kind of genetically programmed cell death and, morphologically, it takes place according to the following processes: aggregation of nucleus; cell contraction; vacuole formation; smoothening of cell surface; expansion of intercellular intervals; liberation of cells from the surroundings; fragmentation of cells (apoptosis corpuscles); and phagocytosis by macrophage, etc. It has also been known that, biochemically, nucleosome unit of DNA is fragmented by endonuclease activity into DNA of base length of 180–200 (Immunology Today, 7:115–119, 1986; Science, 245:301–305, 1989).

At present, it has been clarified that, in addition to physiological functions such as development/differentiation and turnover of normal tissues and cells, this apoptosis participates in certain diseases such as inflammation and reduction of lymphocytes caused by ischemic nerve cell death after cerebral infarction, etc., involution of carcinoma, action of radioactive ray and anticancer agent and infection of virus such as AIDS. Thus, development of drugs for controlling apoptosis (i.e., apoptosis inhibitors and apoptosis inducers) has been expected to give birth to drugs based on new action mechanisms in the broad areas including central nervous system as well as cancer, aging, etc.

With regard to substances and factors for inducing apoptosis, toxicity of neurotransmitters such as glucocorticoid and glutamic acid, irradiation of radioactive ray, NK cells, killer cells, tumor necrosis factor (TNF), cytokines such as lymphotoxin (LT), etc. have been reported. It has also been reported that cycloheximide which is a protein synthesis inhibitor or actinomycin D which is an RNA synthesis inhibitor induces apoptosis to human leukemia cells HL-60. Further, anti-Fas monoclonal antibody to Fas antigen which is a cell membrane molecule participating in apoptosis of immune cells has been prepared recently and various investigations have been conducted for application of anti-Fas antibody to pharmaceuticals.

On the other hand, substances which inhibit interleukin 1 converting enzyme, basic fibroblast growth factor (bFGF), etc. have been reported as factors for inhibiting apoptosis. It has also been known that bcl-2 related gene products inhibit apoptosis and have a macrobiotic function for cells. However, all of those apoptosis inhibiting factors are derived from living organisms and, up to now, no apoptosis inhibitor obtained by industrial means such as chemical synthesis has yet been known.

On the other hand, during the course of investigation of physiological action of brain function in detail, the inventors of the present application have found various isocarbacyclins acting as specific ligands to prostacyslin ruchptor of the central nerve system and have filed patent applications already [Japanese Patent Application Nos. 051,589/96 (JP-A 245,498/96), 243,122/96 (JP-A 87608/98), 260,957/96 (JP-A 101610/98) and 160,320/97]. As a result of further investigation on the physiological activity of those subtances, several of them have been found to show a significant apoptosis inhibiting effect.

Accordingly, an object of the present invention is to offer a novel apoptosis inhibitor which can be manufactured by means of chemical synthesis in large quantities and also at low cost by a further development of the above-mentioned findings by the present inventors.

SUMMARY OF THE INVENTION

The first aspect of the present invention is an apoptosis inhibitor containing as an effective component a 15R-isocarbacyclin derivative represented by the following formula (1).

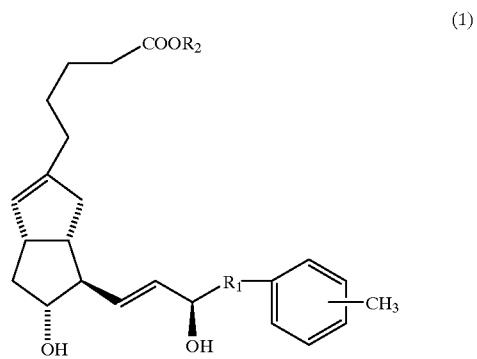

(in the formula, $R_1$ a hydrocarbon chain having 1–6 carbon atom(s),; and $R_2$ is a hydrogen atom or a protective group)

In the apoptosis inhibitor of the first aspect, it is a preferred embodiment that the 15R-isocarbacyclin derivative is 15R-16-(m-tolyl)-17,18,19,20-tetranorisocarbacyclin represented by the following formula (2) a methyl ester thereof.

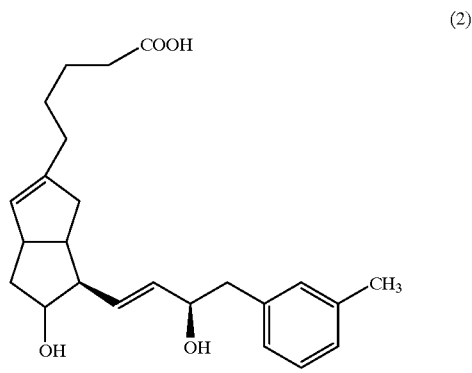

The second aspect of the present invention is an apoptosis inhibitor containing as an effective component a 15-Deoxy-isocarbacyclin derivative represented by the following,; formula (3).

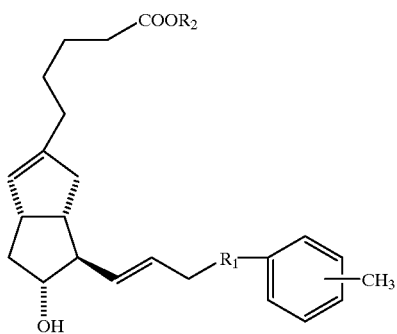

(3)

(in the formula, $R_1$ is a hydrocarbon chain having 1–6 carbon atom(s),; and $R_2$ is a hydrogen atom or a protective group)

In the apoptosis inhibitor of the second aspect, it is a preferred embodiment that the 15-Deoxy-isocarbacyclin derivative is 15-Deoxy-16-(m-tolyl)-17,18,19,20-tetranorisocarbacyclin represented by the following formula (4) or a methyl ester thereof.

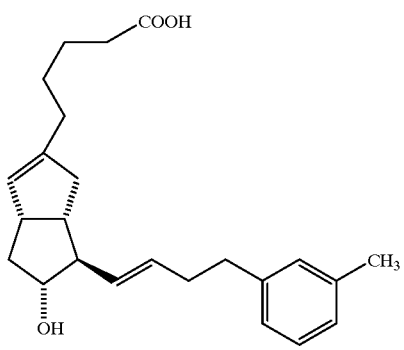

(4)

In the above-mentioned formulae (1) and (3), the protective group which constitutes $R_2$ is a pharmaceutically acceptable salt, ester, etc. and an example is an alkyl group which constitutes a methyl ester, ethyl ester, etc.

Embodiments of the present invention will now be further illustrated as hereunder.

DESCRIPTION OF THE PREFERRED EMBODIMENTS

Figure 1:
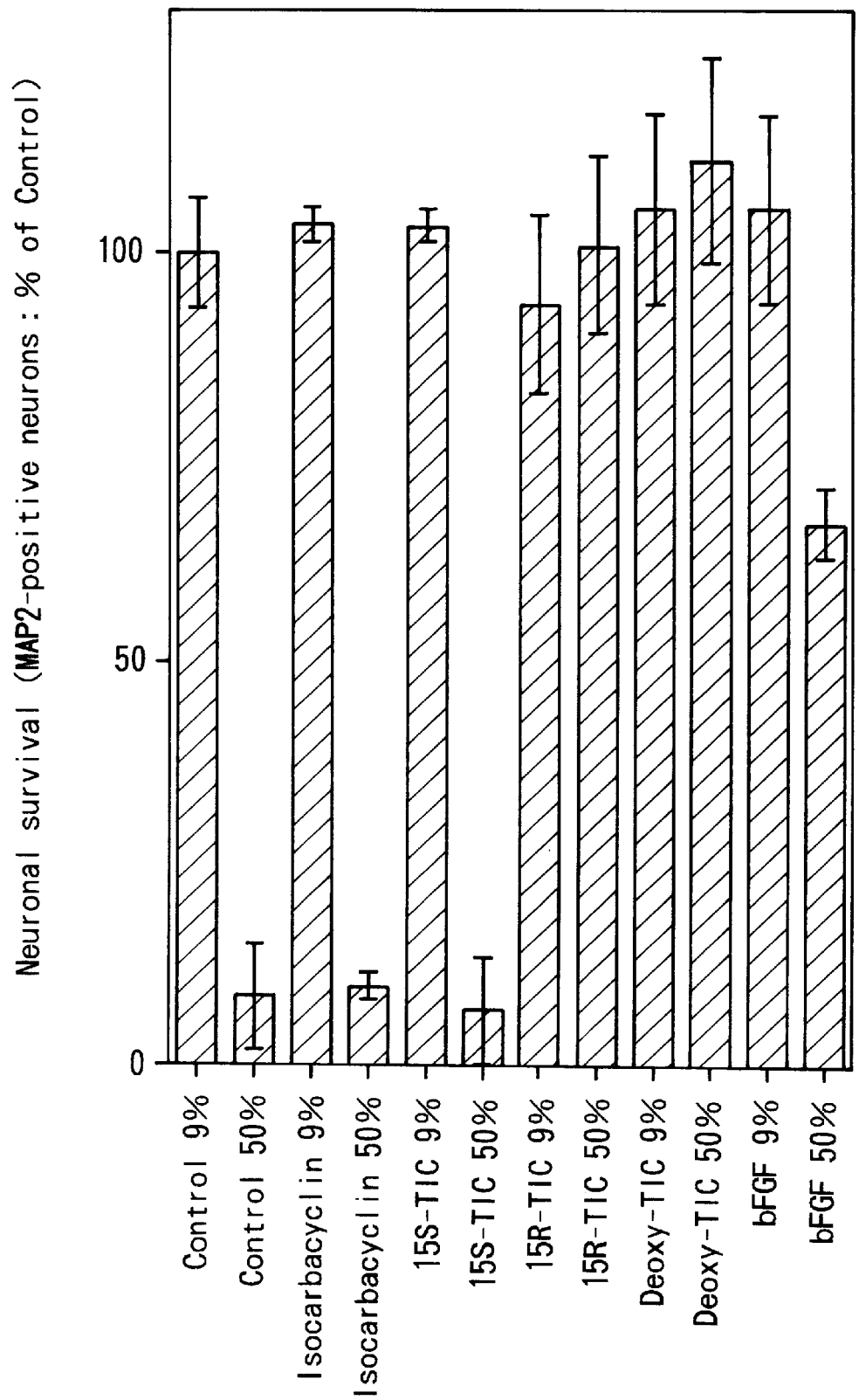
FIG. 1 and 2 are graphs showing th inhibitory effect of the tested samples on apoptosis of hipocampal neuron.

An example of the 15R-isocarbacyclit derivative which is an effective component of the first aspect is 15R-16-(m-tolyl)-14,18,19,20-tetranorisocarbacyclin (hereinafter, may be referred to as "15R-TIC") or a methyl ester thereof, and can be prepared by the method disclosed in JP-A 245,498/96 filed by the present inventors.

The 15-Deoxy-isocarbacyclin derivative which is an effective component of the second aspect is, for example, 15-Deoxy-16-(m-tolyl)-17,18,19,20-tetranorisocarbacyclin (hereinafter, may be referred to as "Deoxy-TIC") or a methyl ester thereof, and can be prepared by the method disclosed in the Japanese Patent Application No. 160,320/97 filed by the present inventors.

The apoptosis inhibitor of the present invention can be made into pharmaceutical preparations containing any of those isocarbacyclin derivatives. In the case of manufacturing a pharmaceutical preparation for applying on the central nervous system, it is preferred to manufacture the preparation with the methyl ester or the like of those isocarbacyclin derivatives. This is because that, as shown in the following Referential Example 2, such a methyl ester or the like is easily taken up into the brain and is converted to an isocarbacyclin derivative such as 15R-TIC or Deoxy-TIC in the brain thereby achieving an inhibiting effect on neural apoptosis. For the purpose of inhibiting the apoptosis in somatic cells, isocarbacyclin derivative such as 15R-TIC or Deoxy-TIC can be used as an effective component of a preparation. In addition to such an effective component, the apoptosis inhibitor of the present invention may further contain known apoptosis inhibiting substances.

The apoptosis inhibitor of the present invention may be administered to human or other animals in a form of common pharmaceutical preparations. For example, it may be administered to human or other animals by means of intravenous injection, subcutaneous injection or oral administration.

The apoptosis inhibitor of the present invention may be made into pharmaceutical preparations containing not less than 5 $\mu$mol/kg of isocarbacyclin derivative together with other components. Examples of said other components are those which are commonly used in the field of manufacture of pharmaceuticals such as diluting agents and vehicles including fillers, bulking agents, binders, moisturizers, disintegrating agents, surface-active agents and lubricants. With regard to a dosage form, various forms may be selected depending upon the object of therapy and representative examples thereof are tablets, pills, diluted powder, liquid, suspension emulsion, granules, capsules, suppositories and injections (in liquid, suspension, etc.).

For example, in the case of preparing the injections, it is preferred that liquid, emulsion and suspension are sterilized and are isotonic to blood. Examples of the applicable diluent are water, ethyl alcohol, propylene glycol, ethoxylated isostearyl alcohol, polyoxylated isostearyl alcohol and polyoxyethylene sorbitan fatty acid esters. In each case, it is also possible to add salt, glucose, glycerol, etc. in such an amount that is satisfactory to prepare an isotonic solution. It is further possible to compound auxiliary solubilizers, buffers, analgetizing agent, etc. therewith.

If necessary, the pharmaceutical Preparations in each of the above-mentioned forms may be further compounded with commonly used coloring agents, preservatives, perfumes, condiments, sweeteners, etc. Other pharmaceutically effective components may be compounded therewith as well.

The present invention will be illustrated in detail and in a specific manner by the following examples although the present invention is not limited to those examples.

EXAMPLE 1

Effect of 15R-TIC and Deoxy-TIC on hippocampal neuron apoptosis induced by a high-oxygen incubation was tested.

(1) Samples

Isocarbacyclin was a pure sample supplied from Teijin Co., Ltd. 15S-TIC was prepared in accordance with the method disclosed in Example 3 of JP-A 245,498/96 by using 15S-16-m-tolyl-17,18,19,20-tetra-nor-carbacyclin which is also disclosed in Example 2 of the same Publication JP-A 245,498/96. The 15R-TIC was prepared by the same method as disclosed in Example 3 of the Publication JP-A 245,498/96. bFGF was the commercially available one.

(2) Procedures

Hippocampal region was cut out from the fetal rat brain which was aseptically isolated from a pregnant rat (Wistar strain) of 20 days of age and the hippocampal region was dispersed into neurons by shaking culture for 30 minutes in a PBS (Ca- and Mg-free) containing DL-cysteine (0.2 mg/ml), bovine serum albumin (0.2 mg/ml), glucose (5 mg/ml), DNase I (0.01%) and papain (9 units/ml). After that, each neutron was planted at the density of $5 \times 10^5$ cells/cm$^2$ on a 24-well plate (coated with polyethyleneimine) filled with a DME/F-12 medium (containing 5% equine serum and 5% fetal bovine serums and incubated for two days in a 5% carbon dioxide gas incubator (9% oxygen). After that, the culture medium was substituted with an DME/F-12 medium (containing 5 µg/ml of transferrin, 5 µg/ml of insulin and 5 nM progasterone) wherefrom serum was removed. Then each sample to be tested was added to the medium, and after 30 minutes, transfered into 50% oxygen. After incubating in 50% oxygen for 48 hours, the survival rate of the neurons was measured. The neurons in 9% oxygen were also added to each sample and the survival rate was measured.

Which regard to the survival rate, the neurons were immobilized by 4% paraformaldehyde, stained with anti-MAP2 antibody and colored by DAB, and the cells positive to MAP2 were counted from the 200-fold enlarged picture whereupon the survival rate was calculated.

(3) Results

FIG. 1 shows the survival rate of hippocampal neurons incubates in 9% or 50% oxygen where bFGF was added at a concentration of 50 nM and other samples were at 5 µM. The number of survived neurons in 9% oxygen was used as a control. When isocarbacyclin or 15S-TIC was added, the survival rate of hippocampal neuron was greatly reduced by apoptosis induced by a high-oxygen condition as same as under the control condition On the contrary, when 15R-TIC or Deoxy-TIC was added, an increase in the survival rate of neurons was observed to the same or even better extent as compared with the case of bFGF which is known as an apoptosis inhibitor in this experimental system.

Figure 2:
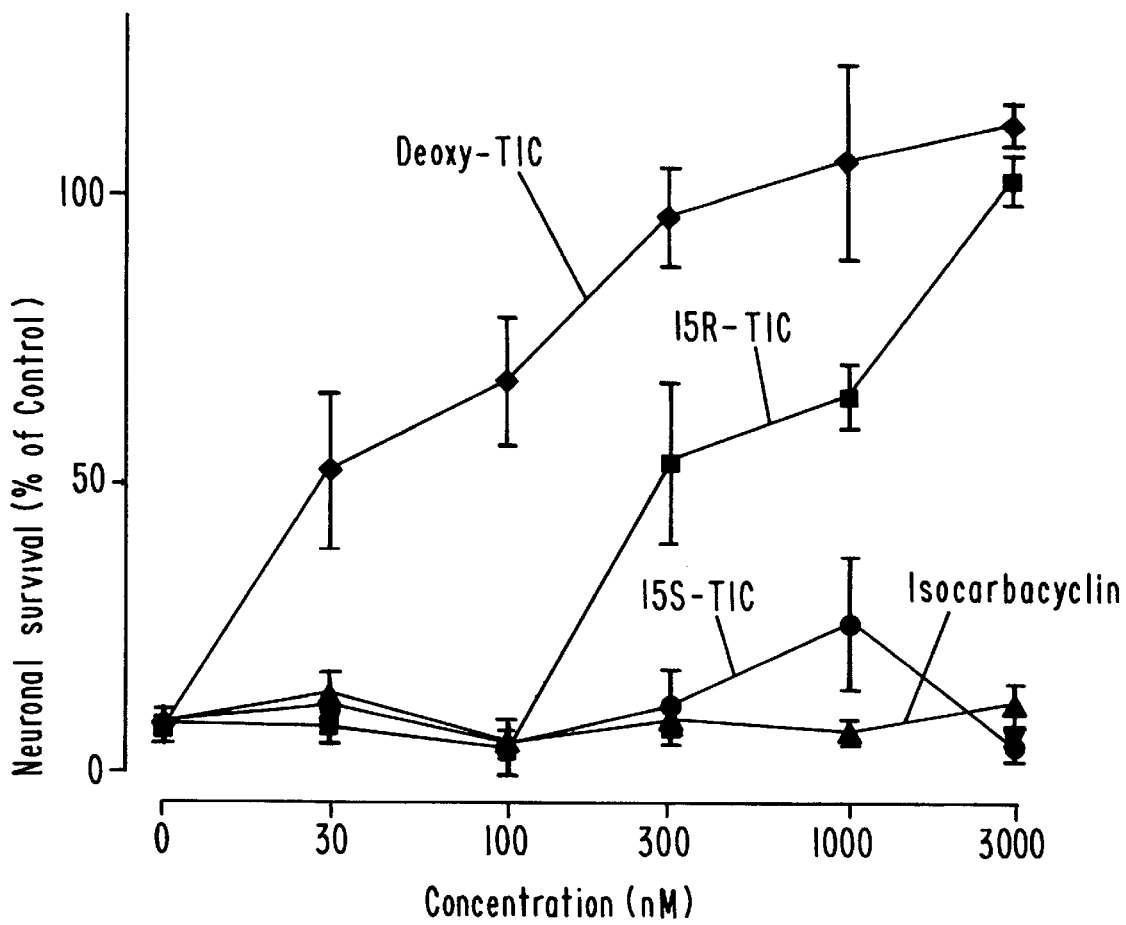

FIG. 2 shows the dose-dependent effects of the tested samples in hippocampal neural apoptosis. In this figure, the survival rate of neurons in 9% oxygen was, used as a control, and the survival rate of neurons to which each sample being added was expressed as the mean ±S.D. (n=4). As is clear from FIG. 2, while isocarbacyclin and 15S-TIC did not have any effect on neuroprotection in the range of concentrations tested, both 15R-TIC and Deoxy-Tic show the dose-dependent inhibitory effect on neural apoptosis, and the survival rate at 3000 nM was equivalent to the control. IC50 values were ca. 30 nM and 300 nM for Deoxy-TIC and 15R-TIC, respectively.

From these results, it has been now ascertained that 15R-TIC and Deoxy-TIC, the effective components of the apoptosis inhibitor of the present invention, exhibit an excellent inhibiting effect to apoptosis of cells, particularly to apoptosis of neurons.

EXAMPLE 2

Effect of 15R-TIC on hippocampal CA1 pyramidal neurons apoptosis induced by ischemic damage in mongolian gerbils was tested in vivo.

To examine whether 15R-TIC can prevent nouronal death in vivo, using an osmotic mini-pomp, 15R-TIC solution was continuously infused for 7 days (started 2 days before the transient ischemia and ended at 5 days) into the left lateral ventricle of gerbils that had been subjected to a transient forebrain ischemia for 3 minutes. Survival number of CA1 pyramidal neurons was assessed by counting neurons with cell bodies larger than 10 µm in the Nissl-staining sections.

Administration of 15R-TIC blocked the loss of CA1 pyramidal neurons induced by forebrain ischemia. The number of neurons in the 15R-TIC-infused gerbils (984±299 in a 20 µm thick section, n=4) was comparable to that in ischemia-free contral gerbils (1061±220, n=4). However, the number of CA1 pyramidal neurons in vehicle-infused gerbilis (142±28, n=4) was significantly less than that of the control (without ischemic treatment) or 15R-TIC-infused gerbils. Pyramidal neurons in the vehicle-infused gerbils has progressively degenerated, with the nuclei having shrunk and the alignment of cells destroyed.

These results indicate that 15R-TIC acts as an effective neuronal survival-promoting factor in vivo, as well as in vitro data shown in Examples 1 and 2.

REFERENTIAL EXAMPLE 1

Figure 3:
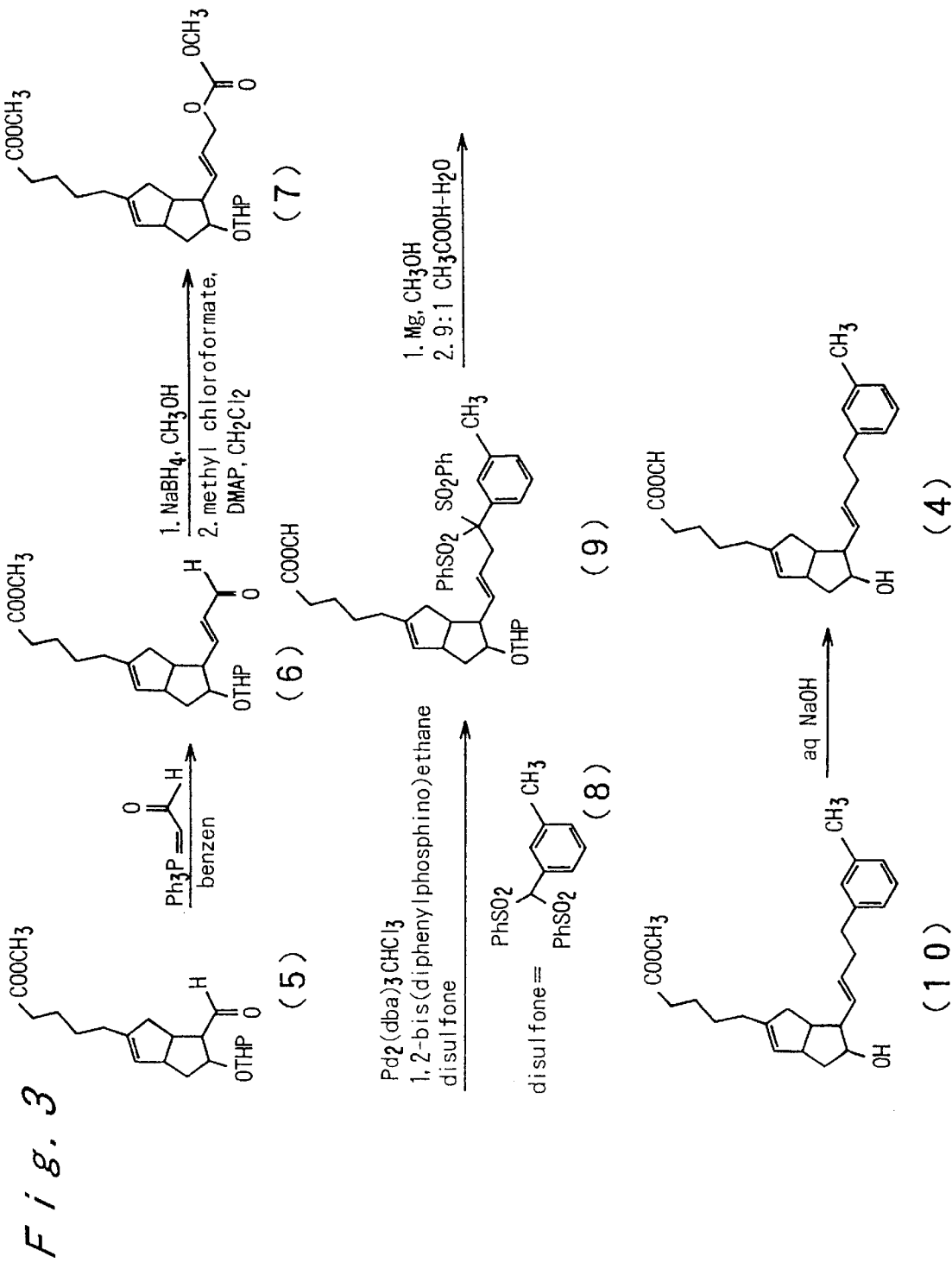
FIG. 3 is a chemical formulae showing the synthetic process pf Deoxy-TIC.

In accordance with the description of Example 1 of the Japanese Patent Application No. 160,320/97, Deoxy-TIC was synthesized as follows, in accordance with FIG. 3.

<1> Synthesis of the Aldehyde Compound (6)

A solution of (triphenylphosphoranylidene) acetaldehyde (21.8 mg 71.6 µmol) in benzene (1.5 ml) was placed in a 10-ml Skulenk tube, then a solution of the above aldehyde compound (5) (23.0 mg, 65.3 µmol) in benzene (1.5 ml) was added thereto and the fixture was heated to reflux for 20 hours. The reaction mixture was cooled, the solvent was evaporated therefrom and the residue was purified by means of an $SiO_2$ chromatography using 2:1 and 1:1 mixtures of hexane and ethyl acetate to give an aldehyde compound (6) (14.8 mg, 61%) The $R_f$ value in the TLC was 0.55 (1:1 mixture of hexane and ethyl acetate).

<2> Synthesis of the Carbonate Compound (7)

A solution of the above aldehyde (6) (7.6 mg, 20.2 µmol) in methanol (1.0 ml) was placed in a 10-ml round-bottom flask, teen $CeCl_7.H_2O$ (10 mg, 27 µmol) and $NaBH_4$ (2 mg, 53 µmol) were added thereto and the mixture was stirred for five minutes. After that, ethyl acetate and waiter were added to the reaction mixture. Extraction was conducted for three times using ethyl acetate as a solvent. The organic phases were combined, dried over $MgSO_4$ and filtered and the filtrate was concentrated in vacuo. The resulting crude product was placed in a 10-ml round-bottom flask and dissolved in $CH_2Cl_2$ (2.0 ml). To this solution were added DMAP (37.0 mg, 0.303 mmol) and methyl chloroformate (0.015 ml, 0.194 mmol) followed by stirring for four hours. After that, an aqueous solution of $NaHCO_3$ was added thereto and the mixture was extracted with ethyl acetate. The organic phases were combined, dried over $Na_2SO_4$ and filtered and the filtrate was concentrated in vacuo. This was purified by means of an $SiO_2$ chromatography using a 4:1 mixture of hexane and ethyl acetate to give the above-mentioned carbonate compound (7) (8.0 mg, 91%). $R_f$ in TLC was 0.42 (2:1 mixture of hexane and ethyl acetate).

<3> Synthesis of the Adduct Compound (9)

A solution of tris (dibenzylideneacetone)-dipalladium (O)-chloroform adduct (2.1 mg, 2.0 µmol) and 1,2-bis (diphtnylphosphino)ethane (1.6 mg, 4.0 µmol) in THF (1.0 ml) was placed in a 20-ml Skulenk tube. To this solution was added a solution of the above carbonate compound (7) (8.0 mg, 18.3 μmol) and disulfone (7.6 mg, 19.7 μmol) in THF (1.0 ml) and the mixture was stirred for 15 minutes. The reaction mixture was poured into an aqueous solution of $NH_4Cl$ followed by extracting with ethyl acetate. The organic phases were combined, dried over $MgSO_4$ and filtered and the filtrate was concentrated in vacuo. This was purified by means of an $SiO_2$ chromatography using 2:1, 1:1 and 1:2 mixtures of hexane and ethyl acetate to give a desired adduct (9) (9.6 mg, 70%). $R_f$ in TLC was 0.27 (1:1 mixture of hexane and ethyl acetate).

<4> Synthesis of the Compound (10): 15-Deoxy-16-(m-tolyl)-17,18,19,20-tetranorisocarbacyclin methyl ester Mg (10 mg, 0.4 mmol) was placed in a 10-ml round-bottom flask and then a solution or the above adduct (9) (7.5 mg, 10.0 μmol) in methanol (1.5 ml) was added followed by stirring for three hours. An aqueous solution of HCl (1N) was added to the reaction mixture followed by extracting with ethyl acetate. The organic phases were combined, dried over $MgSO_4$ and filtered and the filtrate was concentrated in vacuo. The resulting crude product was placed in a 10-ml round-bottom flask and dissolved in a 9:1 mixture (2.0 ml) of acetic acid and water. After stirring for 40 hours, ethyl acetate was added to the solution followed by washing with an aqueous solution of $NaHCO_3$. The organic phase was dried over $Na_2SO_4$ and filtered and the filtrate was concentrated in vacuo. This was then purified by means of an $SiO_2$ chromatography using a 3:1 mixture of hexane and ethyl acetate to give a desired compound (10), i.e., 15-Deoxy-16-(m-tolyl)-17,18,19,20-tetranorisocarbacyclin methyl ester (2.2 mg, 58%). $R_f$ in TLC was 0.6 (1:1 mixture of hexane and ethyl acetate).

<5> Synthesis of the Compound (4): 15-Deoxy-16-(m-tolyl)-17,18,19,20-tetranorisocarbacyclin.

A solution of the above compound (10) (1.0 mg, 2.6 μmol) in methanol (0.5 ml) was placed in a 10-ml test tube, an aqueous solution (3N, 0.2 mol) of NaOH was added thereto and the mixture was stirred at room temperature for 12 hours. $NaHCO_3$ was added thereto and then ethyl acetate and water were further added. The pH was adjusted to 3. The organic phase was separated and the aqueous phase was extracted with ethyl acetate. The organic phases were combined, dried over MgSO4 and filtered and the filtrate was concentrated in vacuo. This was purified by means of an $SiO_2$ (0.5 g) chromatography using a 10:1 mixture of $CH_2Cl_2$ and methanol to give the desired compound (4), the 15-Deoxy-16-(m-tolyl)-17,18,19,20-tetranorisocarbacyclin (0.9 mg, 94%). $R_f$ in TLC was 0.39 (9:1 mixture of $CH_2Cl_2$ and methanol).

REFERENTIAL EXAMPLE 2

Uptake of the isocarbacyclin derivative into brain was measured by means of positron emission tomography (PET).

(1) Samples

[11]C-Labeled 15R-TIC methyl ester (RTA) was prepared by labeling the methyl group carbon at 16-m-tolyl group in the 15R-TIC methyl ester with [11]C. [11]C-Labeled methyl of 15R-TIC (RTC) was prepared by labeling the methyl group carbon at methyl group in the 15R-TIC methyl ester with [11]C. The 15R-TIC methyl ester was prepared by the same method as in Example 2 of JP-A 245498/96.

(2) Procedures

A tracer amount (not more than 0.8 μg/kg) of the above mentioned sample was intravenously injected to an adult rhesus monkey (body weight being about 8 kg) and the behavior of the sample in the brain from the intravenous injection until 60 minutes thereafter was imaged by means a PET device. ROI (region of interest) was calculated from said image and the uptake amount was calculated by the following formula.

Uptake Amount=[(Calculated Weight of ROI in Brain)/(Body Weight)]÷[(RI Counts Accumulated in ROI)/(Administered RI Counts)]

(3) Results

Figure 4:
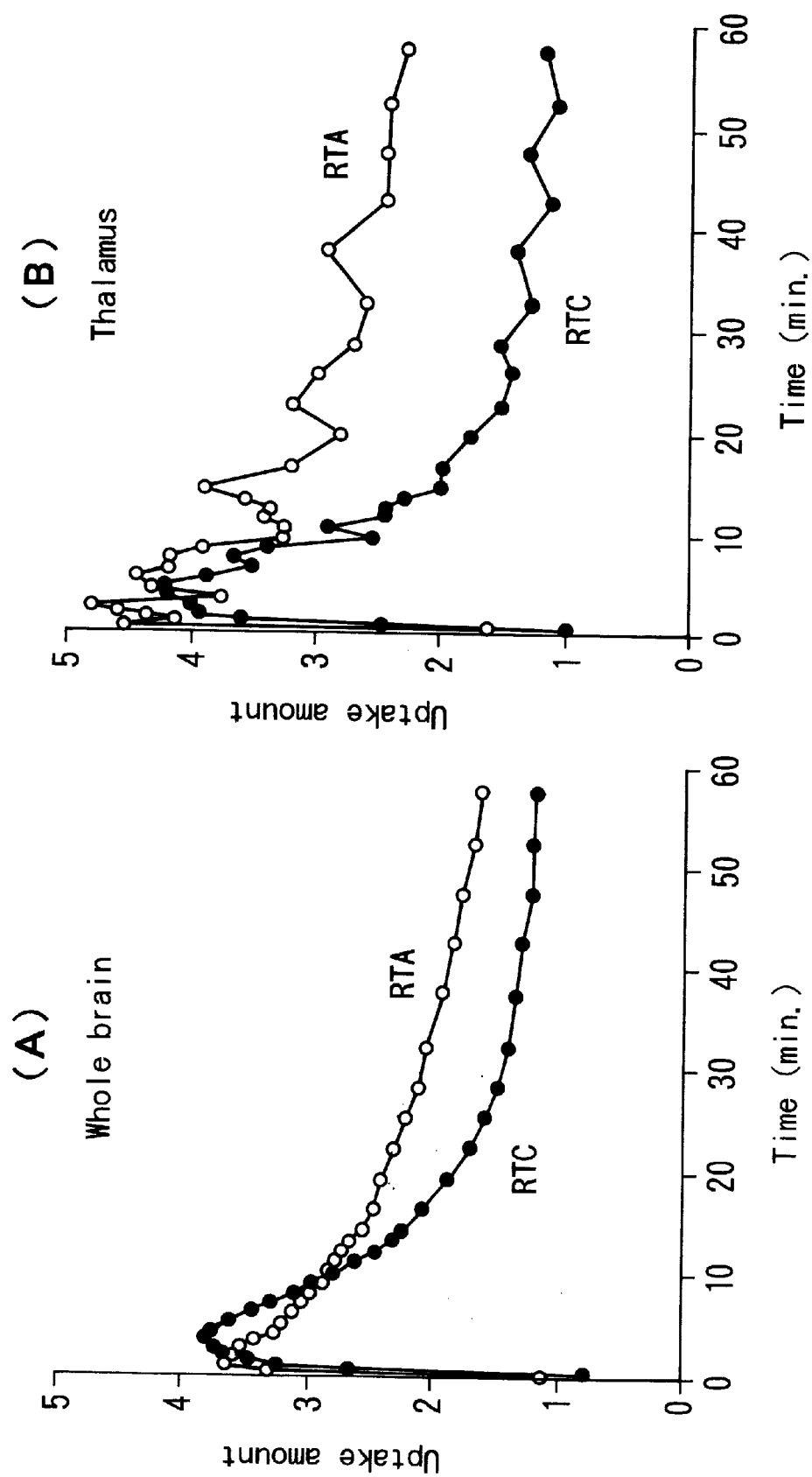
FIG. 4(A) and (B) are graphs showing uptake of labeled isocarbacyclin derivatives in whole train and thalamus, respectiely.

FIG. 4(A) shows the incorporated amount of each of the labeled compounds in the whole brain and FIG. 4(B) shows the incorporated amount in the thalamus. RTA and RTC showed equivalent pass through blood-brain-barrier (FIG. 4A and B), but RTA retained in the brain further than RTC, indicating the retention of deesterified [11]C-Labelled 15-TIC in the brain. In other words, RTA could serve as a prodrug for 15R-TIC. It is clear from those results that the 15-TIC methyl ester systemically administered has been confirmed to be efficiently transfererd into the brain. Since the labeled compound remains in the brain for not shorter than 60 minutes after the administration, it has been suggested that the 15R-TIC methyl ester (a precursor to 15R-TIC) is converted to 15R-TIC in the brain to bind to prostacyclin receptor and that its apoptosis inhibiting action is achieved in the brain.

According to the present invention, a novel apoptosis inhibitor, of which ingredient is a compound available easily and economically by means of chemical synthesis, is provided. It has been clarified by PET study that the isocarbacyclin derivative, an effective component of the apoptosis inhibitor, passes through the blood-brain-barrier and acts on the central nervous system and, accordingly, the inhibitor is particularly effective for the therapy of various diseases caused by neural apoptosis.

What is claimed is:

1. An apoptosis inhibitor comprising as an effective component a 15-Deoxy-isocarbacyclin derivative represented by the following formula

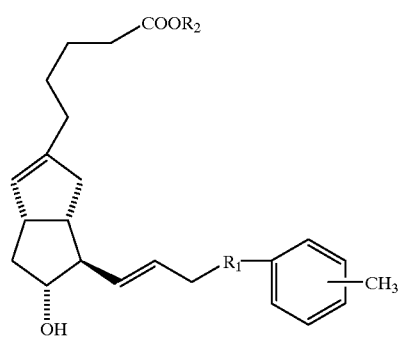

wherein $R_1$ is a hydrocarbon chain having 1–6 carbon atom(s), and $R_2$ is a hydrogen atom or a protective group.

2. The apoptosis inhibitor of claim 1, wherein the 15-deoxy-isocarbacyclin derivative is 15-Deoxy-16-(m-tolyl)-17, 18, 19, 20-tetranorisocarbacyclin represented by the following formula or a methyl ester thereof.

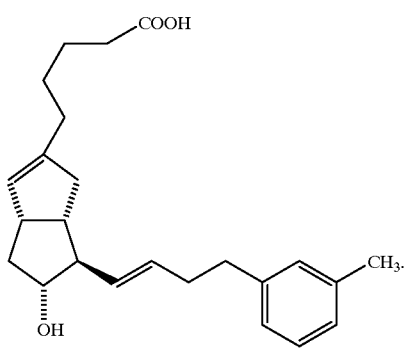

3. A method for inhibiting apoptosis comprising administering as an effective component a composition comprising 15R-isocarbacyclin derivative represented by the following formula to the cells of an animal suffering abnormal cell death due to apoptosis

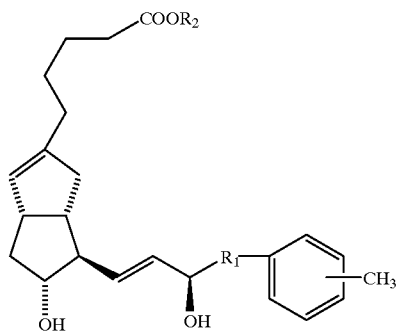

wherein $R_1$ is a hydrocarbon chain having 1–6 carbon atom(s), and $R_2$ is a hydrogen atom or a protective group.

4. The method for inhibiting apoptosis according to claim 3, wherein the 15R-isocarbacyclin derivative is 15R-16-(m-tolyl)-17, 18, 19, 20-tetranorisocarbacyclin represented by the following formula or a methyl ester thereof

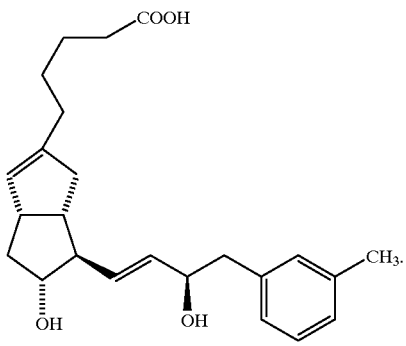

5. The method for inhibiting apoptosis according to claim 3, wherein the animal is a human.

6. The method for inhibiting apoptosis according to claim 4, wherein the animal is a human.

* * * * *